United States Patent [19]

Hertl

[11] 3,977,982

[45] Aug. 31, 1976

[54] CONTROLLING VISCOSITY OF SILICA-SILICONE OIL GELS

[75] Inventor: William Hertl, Corning, N.Y.

[73] Assignee: Corning Glass Works, Corning, N.Y.

[22] Filed: Jan. 20, 1975

[21] Appl. No.: 542,488

[52] U.S. Cl. .......................... 252/60; 210/DIG. 23; 252/316
[51] Int. Cl.² ........................................... C09K 3/00
[58] Field of Search ............... 252/60, 316; 210/83, 210/516, DIG. 23

[56] References Cited
UNITED STATES PATENTS

| | | | |
|---|---|---|---|
| 3,780,935 | 12/1973 | Lukacs et al. | 210/83 X |
| 3,852,194 | 12/1974 | Zine | 210/83 |

*Primary Examiner*—Harris A. Pitlick
*Attorney, Agent, or Firm*—James A. Giblin; Clinton S. Janes, Jr.; Clarence R. Patty, Jr.

[57] ABSTRACT

The viscosity of a silica-silicone oil gel-like composition useful as a partitioning substance in blood collection tubes can be controlled by first preparing a mixture of a silicone oil and silica particles to form a mixture having a viscosity greater than about 200,000 centistokes, reacting the mixture in an evacuated environment at a temperature ranging from about 175° to 550°C. for a period of time sufficient to reduce the viscosity below about 120,000 centistokes, and then adding a network former to the reaction mixture in a quantity sufficient to increase the viscosity to a range of about 200,000 to 600,000 centistokes, preferably to a range of about 350,000 to 450,000 centistokes.

5 Claims, No Drawings

CONTROLLING VISCOSITY OF SILICA-SILICONE OIL GELS

RELATED APPLICATION

Patent application Ser. No. 532,946, filed Dec. 16, 1974 in the name of A. R. Zine, entitled "Stabilized Blood Separating Composition", and assigned to the present assignee.

BACKGROUND OF THE INVENTION

1. Field

This invention is concerned generally with thixotropic gel-like compositions which are used to assist in the separation and partitioning of whole blood into serum and clot portions. Specifically, the invention is concerned with methods of preparing such compositions in a manner which permits an effective and convenient control of viscosity.

2. Prior Art

The specific gravity of whole human blood is generally within the range of about 1.048 to 1.066. It has long been known that such blood can be readily centrifuged to effect a separation of the blood into two major components—a lighter serum portion having a specific gravity within the range of about 1.026 to 1.031 and a heavier clot portion, consisting mainly of red blood cells, having a specific gravity within the range of about 1.092 to 1.095. Such separations of blood into its two major portions are commonly used to facilitate physical and chemical analyses of blood. Such analyses are helpful in the diagnosis and prognosis of many human ailments.

With the advent of modern techniques for the analyses of various physical and chemical sub-components of blood, there has been a general recognition that simple centrifugation of blood into its two major components does not necessarily effect an ideal separation for analytical purposes. For example, even though simple separation yields a gross separation of whole blood into serum and clot portions, there still exists an interface between the separated portions which, especially with time, results in diffusion of various sub-components of one separated portion into the other. Such diffusion can affect the accuracy of various analyses.

In recent years, considerable efforts have been made to modify simple centrifugation techniques so that the formation of a serum-clot interface is avoided. For example, it is now well known that certain gel-like, essentially inert, thixotropic substances, having a specific gravity intermediate those of the serum and clot portions, can be used to assist in the separation and partitioning of serum and clot portions. One such substance comprises a viscous gel-like material consisting of a silicone fluid having inert siliceous particles dispersed therein in an amount sufficient to yield a specific gravity in the range of about 1.030 to about 1.050. When whole blood, contained in a test tube, is centrifuged in the presence of such a substance, the gel-like material, because of its thixotropic nature and specific gravity, tends to migrate to a position intermediate those of the serum and clot portions and ultimately assume a configuration and position which discourages and prevents the formation of a serum-clot interface by acting as a physical and chemical barrier.

Various examples of such silica-silicone fluid composition are well known in the art and described more fully, for example, in U.S. Pat. No. 3,780,935 to Lukacs and Jacoby; U.S. Pat. No. 3,852,194 to Zine; and patent application Ser. No. 532,946 cited above as a related application. In the two cited patents, preferred compositions consist essentially of a silicone fluid such as a dimethylpolysiloxane having very fine silica particles dispersed therein to achieve a desired specific gravity. More recently, in patent application Ser. No. 532,946, it was disclosed that such compositions can be stabilized to avoid "wet out" through the addition of relatively minute amounts of certain polysiloxane-polyoxyalkyl copolymers which act as network formers between the dispersed silica particles.

Very generally, the expression "wet out" refers to the tendency of such compositions to lose viscosity with time. Such loss in viscosity results in a loss in the gel-like nature of the composition and the relative firmness of the composition is lessened. A very undesirable effect of wet out occurs when an attempt is made to pour off the upper serum portion of separated blood contained in a test tube. For example, as long as the test tube containing separated blood is maintained in an essentially vertical position a wetted out barrier generally poses no particular problem. However, as the tube is tilted to pour off the upper serum portion, a wetted out barrier has a tendency to slump, thereby disturbing the previously maintained seal between the serum and clot portions. As the seal is disturbed, there forms an interface between the serum and clot portions, thus permitting diffusion of various sub-components of blood and adversely affecting certain analyses. It is also recognized that the undesired slumping due to wet out can occur even if a test tube containing the separated blood is jarred. Hence, as described in greater detail in patent application Ser. No. 532,946, the use of certain network formers in silica-silicone fluid compositions provides a practical method for stabilizing such compositions against wet out (or viscosity loss) for periods of up to and greater than one year.

The occurrence of wet out is thought to be due to a complete interaction of the silica surfaces with the silicone fluid over a period of time. Although the silica particle fillers are often described as being essentially inert, it is known that the surfaces of such particles have available hydroxyl groups capable of interaction with the silicone fluid. The use of certain network formers tends to minimize such surface interaction and, thus, preclude wet out of the particles by assuring that the surfaces of the particles are not completely enveloped by the silicone fluid. It is thought that the network formers tend to compete with the silicone fluid for surface sites on the particles.

In using network formers to stabilize silica-silicone fluid compositions, however, it is recognized that the addition of the network formers has a dramatic effect in increasing the viscosity of the composition. Hence, very small amounts of network former must be used to achieve a stable and controlled viscosity in a range useful for blood separating applications; e.g., about 200,000 to 600,000 centistokes, preferably 350,000 to 450,000 centistokes. As can be seen from Ser. No. 532,946, the amounts of certain polysiloxane-polyoxyalkyl copolymer network formers used to stabilize such silica-silicone fluid compositions were in the range of about 0.0173 to 0.0117 parts by weight. Because such small amounts are used, it is a common practice to carefully titrate the network former into the silica-silicone fluid mixture to achieve a viscosity within a given range.

Although one way of avoiding the tight control of such small amounts of network former involves the use of "methylated" silica particles (having less surface sites available for interaction with the network former and thereby permitting use of larger amounts), it can be appreciated that commercially available "methylated" silica is, in fact, only partially methylated, and it would be fortuitous to obtain a commercially available silica with exactly the desired degree of methylation for this application. It can be appreciated that the preparation of the overall composition involves at least three or more processing steps—e.g., preparing or acquiring a partially methylated silica, mixing it with a silicone fluid, a possible degassing step, a possible dehydration step, and also the addition of an appropriate amount of network former if wet out is to be avoided.

I have found that the processing steps and costs associated with the preparation of such silicone fluid-silica compositions can be effectively reduced and that it is possible to add conveniently varying amounts of network formers to stabilize such compositions. My method of preparing such compositions are described in detail below.

SUMMARY OF THE INVENTION

My method of preparing a thixotropic gel-like material useful as a partitioning substance between the serum and clot portions of blood comprises the steps of:

a. preparing a mixture of a silicone fluid and silica particles to form a gel-like composition having a specific gravity in the range of about 1.030 to 1.090 and a viscosity above about 200,000 centistokes, but less than about 1,000,000 centistokes;

b. reacting the mixture in an evacuated environment at a temperature range of about 175° to 550°C. for a period of time sufficient to reduce the viscosity to less than about 120,000 centistokes by reacting a portion of the surfaces of the silica particles with the silicones fluid; and c. adding a quantity of network former to the reaction products in an amount sufficient to raise the viscosity of the reaction products to a range of about 200,000 to about 600,000 centistokes.

In preferred embodiments, the silicone fluid consists of a dimethylpolysiloxane fluid having a viscosity in centistokes ranging from about 1000 to 12,500, the silica particles consist of finely-divided silica particles having a surface area of at least about 80 m²/g, and the network former is a substance selected from the group consisting of water, ethylene glycol, and a polysiloxane-polyoxyalkyl copolymer of the type described below.

SPECIFIC EMBODIMENTS

A very essential step in my method involves the reaction of the silica particles with the silicone fluid in an evacuated environment at a temperature ranging from 175° to 550°C. to reduce the viscosity to below about 120,000 centistokes. This critical step permits an in situ partial deactivation of the silica surfaces and simultaneously removes all gas and water from the system, thereby eliminating the need for separate dehydration and degassing steps. Further, by allowing the reaction to proceed for a period of time sufficient to reduce the viscosity to below 120,000 centistokes, perferably no lower than about 50,000 centistokes, it is possible to assure only the partial deactivation of the surface. It is essential that the surfaces are not completely deactivated since such complete deactivation would preclude formation of a useful gel-like material for this application. However, a partial deactivation permits conveniently varying amounts of network former to be added. This, coupled with the elimination of a degassing and dehydration step, significantly reduces processing time and costs.

Although the exact mechanism whereby the reaction of the silicone oil and silica surface proceeds is not fully understood, it is thought that in an evacuated environment (e.g., pressure reduced to less than 3 to 4 mm. of Hg) at a temperature range of 175° to 550°C., the silicone oil reacts with the surface hydroxyl groups of the silica by a cleaving of the silicone oil chain in the following manner:

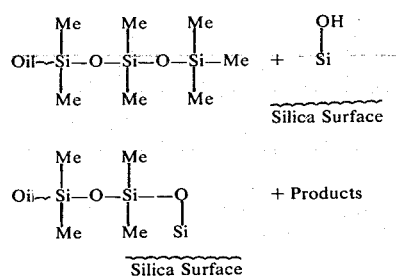

By reacting the silicone fluid and silica under the above-described conditions, there occurs a partial in situ surface deactivation of the silica surfaces and it is thought that such partial deactivation results in a silicone fluid-silica composition which is not very responsive to the addition of network formers or surfactants. Hence, conveniently varying amounts may be added to control the ultimate viscosity and assure that the viscosity can be readily raised to a range of about 200,000 to 600,000 centistokes.

It has been found that below about 175°C. the reaction takes a very long time. Various temperatures and times up to about 500°-550°C. for 5 minutes were used. At the higher temperatures, however, care must be taken to assure that the vaporized oil returns to the heated gel (e.g., by refluxing) so as not to change the specific gravity of the gel which, as noted above, must be within the range of about 1.030 to 1.090, preferably about 1.035 to 1.050. The reaction must proceed until the viscosity is reduced The above about 200,000 to below about 120,000 centistokes. Then, to bring the viscosity back up to about 200,000 to 600,000, preferably 350,000 to 450,000 centistokes, network formers may be added in sufficient quantities, the respective amounts of which depending on the network former used.

Among the network formers found useful are water, glycerol, glycols, polyfunctional amines, and certain polysiloxane-polyoxyalkylsilicone copolymers (e.g., of the type described in Ser. No. 532,946). Those copolymers can be made in a variety of ways and are available commercially, for example, as DC-190, DC-192, and DC-194 surfactants available from Dow Corning Corp., Midland, Michigan.

Such copolymers have the following structure:

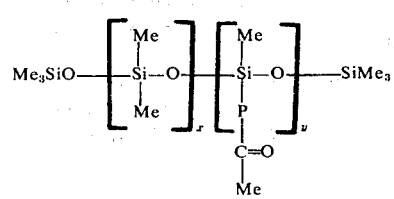

where the monomeric units are randomly distributed and

Me represents —CH$_3$;

$x$ represents a number between 80 and 120;

$y$ represents a number between 8 and 12;

P represents a polyoxyalkyl side chain represented by the formula

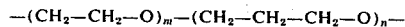

where the monomeric units are randomly distributed and $m$ represents a number between 20 and 30; and $n$ represents a number between 1 and 30.

In the specific examples below, the reagents used were:

| | |
|---|---|
| silica | Degussa Aerosil R-972 (a fumed, methylated silica) |
| | Degussa D-17 (a precipitated, methylated silica) |
| silicone fluid | Dow Corning 360 series silicone fluid, viscosity 1000 centistokes |
| | Dow Corning 200 series silicone fluid, viscosity 12,500 centistokes |
| | Union Carbide L-45 silicone fluid, viscosity 12,500 centistokes |
| network formers | water |
| | ethylene glycol |
| | DC-190 (polysiloxane-polyoxyalkyl copolymer) |

The preferred methods of preparing the compositions are shown in the examples.

EXAMPLE 1

An amount of 680 grams of the Degussa R-972 silica was blended into 4000 g of the DC-360 series silicone fluid having a viscosity of 1000 centistokes to give a gel having a specific gravity of 1.048 and a viscosity of about 500,000 centistokes. This gel was placed in a reactor and heated at 250°C. for a period of 30 minutes with the pressure being maintained at about 2 mm. Hg or less by means of a conventional vacuum system. At the end of the treatment and upon cooling, the treated gel had a viscosity of 85,000 centistokes. To this gel was added 0.15% by weight of the DC-190 copolymer which produced a stabilized gel with a viscosity of 310,000 centistokes.

The reactor used in this and the following examples was a cylindrical steel vessel (approximately 1-½ gallon total capacity) having heating coils wound around the outside. The vessel had a vacuum tight top opening for insertion of a stirrer assembly, the stirring portion of which facilitated degassing and heat transfer.

EXAMPLE 2

An amount of 600 grams of the D-17 silica was blended into 4000 g of the L-45 silicone fluid having a viscosity of 12,500 centistokes to give a gel having a specific gravity of 1.040 and a viscosity of 180,000 centistokes. This gel was placed in the reactor and heated at 210°C. for a period of 30 minutes with the pressure being maintained at about 2 mm. Hg or less by means of a conventional vacuum system. At the end of the treatment and upon cooling, the treated gel had a viscosity of 95,000 centistokes. To this gel was added 0.16% by weight of ethylene glycol which produced a stabilized gel with a viscosity of 300,000 centistokes.

EXAMPLE 3

An amount of 600 grams of the D-17 silica was blended into 4000 g of the DC-360 series silicone fluid having a viscosity of 12,500 centistokes to give a gel having a specific gravity of 1.039 and a viscosity of 240,000 centistokes. This gel was placed in the reactor and heated at 200°C. for a period of 30 minutes with the pressure being maintained at about 2 mm. Hg or less by means of a conventional vacuum system. At the end of the treatment and upon cooling, the treated gel had a viscosity of 80,000 centistokes. To this gel was added 0.3% by weight of water wich produced a gel with a viscosity of 320,000 centistokes.

EXAMPLE 4

An amount of 680 grams of the D-17 silica was blended into 4000 g of the DC-360 series silicone fluid having a viscosity of 12,500 centistokes to give a gel having a specific gravity of 1.048 and a viscosity of 350,000 centistokes. This gel was placed in the reactor and heated at 200°C. for a period of 30 minutes with the pressure being maintained at about 2 mm. Hg or less by means of a conventional vacuum system. At the end of the treatment and upon cooling, the treated gel had a viscosity of about 100,000 centistokes. To this gel was added 0.10% by weight of DC-190 which produced a stabilized gel with a viscosity of 450,000 centistokes.

EXAMPLE 5

An amount of 600 grams of the D-17 silica was blended into 4000 g of the DC-360 series silicone fluid having a viscosity of 12,500 centistokes to give a gel having a specific gravity of 1.039 and a viscosity of 240,000 centistokes. This gel was placed in the reactor and heated at 175°C. for a period of 30 minutes with the pressure being maintained at about 2 mm. Hg or less by means of a conventional vacuum system. At the end of the treatment and upon cooling, the treated gel had a viscosity of about 100,000 centistokes. To this gel was added 0.06% by weight of the DC-190 copolymer which produced a stabilized gel with a viscosity of 410,000 centistokes.

The effect of temperature is illustrated in the table. For the composition given in Example 5, using a fixed percentage (0.10%) of the added network former, and fixed reaction time (30 minutes), the following viscosities were obtained of the stabilized gel.

TABLE

| Thermal Deactivation Temperature | Viscosity in Centistokes |
|---|---|
| None | 725,000 |
| 150°C. | 540,000 |
| 175°C. | 450,000 |
| 200°C. | 400,000 |
| 220°C. | 345,000 |
| 240°C. | 200,000 |
| 300°C. | 140,000 |

It can be appreciated that at the higher temperatures, a reduced reaction time is required to result in an ultimate viscosity within the required 200,000 – 600,000 centistokes range.

From the foregoing various practical advantages can be appreciated. These advantages can be summarized as follows:

1. in cases where water is not used as a network former, the removal of a competing, short chain network former (water);

2. due to the method of processing, the viscosity of the gel is very low (about 120,000 centistokes or lower) before the addition of the network former, which permits easy dispersal of the filler in the oil without expensive equipment;

3. due to the method of processing, dissolved air is readily removed (gel is degassed) from the gel prior to the addition of the network former due to the use of an evacuated environment and the low viscosity; this eliminates a separate degassing step so that the gel is ready for dispensing; and 4. the partial deactivation of the filler, due to the chemical reaction of the filler with the oil, allows greater control in obtaining the desired viscosity.

It should be noted that the above examples are merely illustrative of preferred methods of preparing the gel-like compositions. Accordingly, it can be appreciated that there are some modifications that can be made by one skilled in this art without departing from the spirit and scope of this disclosure.

I claim:

1. A method of preparing a thixotropic gel-like material useful as a partitioning substance between the serum and clot portions of blood, the method comprising the steps of:
   a. preparing a mixture of a silicone fluid and silica particles to form a gel-like composition having a specific gravity in the range of about 1.030 to 1.090 and a viscosity above about 200,000 centistokes;
   b. reacting the mixture in an evacuated environment at a temperature ranging from about 175° to 550°C. for a period of time sufficient to reduce the viscosity to less than about 120,000 centistokes by reaction of a portion of the silica particle surfaces with the silicone fluid; and
   c. adding a quantity of network former to the reaction products of step (b) to raise the viscosity of the reaction products to a range of about 200,000 to about 600,000 centistokes.

2. The method of claim 1 wherein the silicone fluid consists of a dimethylpolysiloxane having a viscosity ranging from 1000 to 12,500 centistokes, the silica particles consist of finely divided silica particles having a surface area of at least 80 m²/gram, and the network former is selected from the group consisting of water, ethylene glycol, and a polysiloxane-polyoxyalkyl copolymer.

3. The method of claim 2 wherein the polysiloxane-polyoxyalkyl copolymer has the following structure

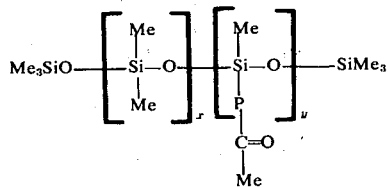

where the monomeric units are randomly distributed and

Me represents -CH₃;

$x$ represents a number between 80 and 120;

$y$ represents a number between 8 and 12;

P represents a polyoxyalkyl side chain represented by the formula

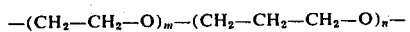

where the monomeric units are randomly distributed and $m$ represents a number between 20 and 30; and $n$ represents a number between 1 and 30.

4. The method of claim 2 wherein the viscosity of the mixture of step (a) is between about 200,000 and 1,000,000 centistokes, the reduced viscosity of step (b) is between 50,000 and 120,000 centistokes, and the final viscosity of step (c) is between about 350,000 and 450,000 centistokes.

5. The method of claim 1 wherein the evacuated environment of step (b) comprises an environment evacuated to a pressure of less than 4 mm. of Hg.